United States Patent [19]
Craine et al.

[11] Patent Number: 5,791,346
[45] Date of Patent: Aug. 11, 1998

[54] COLPOSCOPE DEVICE AND METHOD FOR MEASURING AREAS OF CERVICAL LESIONS

[75] Inventors: Eric R. Craine, Tucson, Ariz.; Brian L. Craine, Fairfax, Calif.

[73] Assignee: Western Research Company, Inc., Tucson, Ariz.

[21] Appl. No.: 670,321

[22] Filed: Aug. 22, 1996

[51] Int. Cl.$^6$ .................................................. A61B 5/00
[52] U.S. Cl. .................... 128/653.1; 128/922; 356/376; 382/285
[58] Field of Search ............... 128/653.1, 920, 128/922, 664, 665, 633; 356/376, 377, 378, 379, 421, 248, 255; 348/65, 68, 77, 136; 382/169, 170, 174, 206, 274, 285, 286, 312, 314, 322

[56] References Cited

U.S. PATENT DOCUMENTS

| | | | |
|---|---|---|---|
| 4,535,782 | 8/1985 | Zoltan | 128/665 |
| 4,556,057 | 12/1985 | Hiruma et al. | 128/303.1 |
| 4,834,070 | 5/1989 | Saitou | 128/6 |
| 4,917,492 | 4/1990 | Koishi | 356/300 |
| 4,998,971 | 3/1991 | Fukunishi | 128/6 |
| 5,003,977 | 4/1991 | Suzuki et al. | 128/633 |
| 5,036,853 | 8/1991 | Jeffcoat et al. | 128/634 |
| 5,080,477 | 1/1992 | Adachi | 351/212 |
| 5,090,400 | 2/1992 | Saito | 128/6 |

*Primary Examiner*—Marvin M. Lateef
*Assistant Examiner*—Shawna J. Shaw
*Attorney, Agent, or Firm*—Cahill, Sutton & Thomas P.L.C.

[57] ABSTRACT

The area of a three-dimensional lesion on a cervix is determined from a two-dimensional image thereof produced by a digital colposcope. A stored reference cervix reflectance map including slant angles and corresponding gray scale intensity levels represents a reference cervix, and is obtained using a shape-assuming target including thereon an array of circular spots of a first reflectivity and a stiff target having thereon a first circular spot of the first reflectivity and a second circular spot of a second reflectivity. An identical stiff target is placed on the cervix, and a two-dimensional image of the lesion and the stiff target is obtained from the digital colposcope. Resulting intensities of the two-dimensional image are calibrated to the gray scale of a standard target reflectance map, and the calibrated intensities of the two-dimensional image are correlated to the intensities of the reference cervix reflectance map to determine slant angles of predetermined points of the cervix. Pixel dimensions of each pixel in the lesion then are corrected in accordance with the slant angles. The lesion area is computed by summing the areas of the pixels with corrected dimensions.

17 Claims, 3 Drawing Sheets

COLPOSCOPE DEVICE AND METHOD FOR MEASURING AREAS OF CERVICAL LESIONS

BACKGROUND OF THE INVENTION

The invention relates to an apparatus and method for accurately computing an area on a three-dimensional object from two-dimensional image data obtained by means of a camera, such as one associated with a digital colposcope.

The HPV virus (human papilloma virus), which produces genital warts, is well known to cause or accelerate development of pre-cancerous or cancerous tissue of the cervix. HPV is a sexually transmitted disease, the widespread incidence of which is approaching epidemic proportions.

Early detection of HPV lesions allows simple, effective treatment by laser surgery, freezing, or chemical exfoliation. The initial appearance of an HPV lesion ordinarily does not call for any surgical treatment, because small lesions frequently disappear if left alone because of the action of a woman's immune system, if it is healthy. Most gynecologists make decisions whether to surgically treat or otherwise remove the lesions based on whether they believe that the lesion is growing or shrinking. However, it is very difficult to accurately determine if the lesion is growing or shrinking.

Previous techniques for determining the progression of a lesion of the cervix include forming of a subjective opinion by the examining physician as to whether the lesion size has changed since a previous examination based on the physician's viewing of the lesion. Typically, present photographs of the lesion, made by means of a colposcope, are compared with a corresponding prior photograph. More recently, computerized measurement of the area has been performed using a colposcope to obtain a video image of the cervix and processing the video image data. However, measurements or computations of the area of a three-dimensional object from a two-dimensional image such as a photograph or a digitized two-dimensional image taken by means of a CCD camera inherently contain inaccurate representations of lesion areas if the lesions are growing on sloped areas of the cervix, in which case a particular lesion may be interpreted as unchanging or decreasing in size when actually it is increasing in size and hence may be dangerous.

Colposcopy is a well known technique of using a colposcope for visualizing the cervix under magnification. By using a speculum to spread the walls of the vagina to allow direct illumination and visualization of the cervix the gynecologist can use a colposcope to directly visualize HPV lesions. However, what the gynecologist sees using the colposcope is a two-dimensional view of a three-dimensional lesion. Depending on the viewing angle of the colposcope relative to the slope of the portion of the cervix on which the lesion occurs, the physician often can see only a "side view" of the lesion which usually prevents an accurate estimate or measurement of how large the surface area of the lesion is. In this case, large increases in the area of the HPV lesion over a period of time cannot be reliably determined from the two-dimensional views of the lesion permitted by the colposcope at the beginning and end of such period of time.

The closest prior art colposcopes, called "digital imaging colposcopes", were developed by the present inventors. A digital imaging colposcope projects the image of the cervix received by the colposcope into an attached CCD camera, using a beamsplitter that reflects part of the cervix image light into the CCD camera. The output of the CCD camera is digitized for each pixel of the CCD camera detector and input to a computer that performs various digital image processing operations on the image data to enhance the cervix image and/or make quantitative measurements of the features of the cervix.

Figure 5:
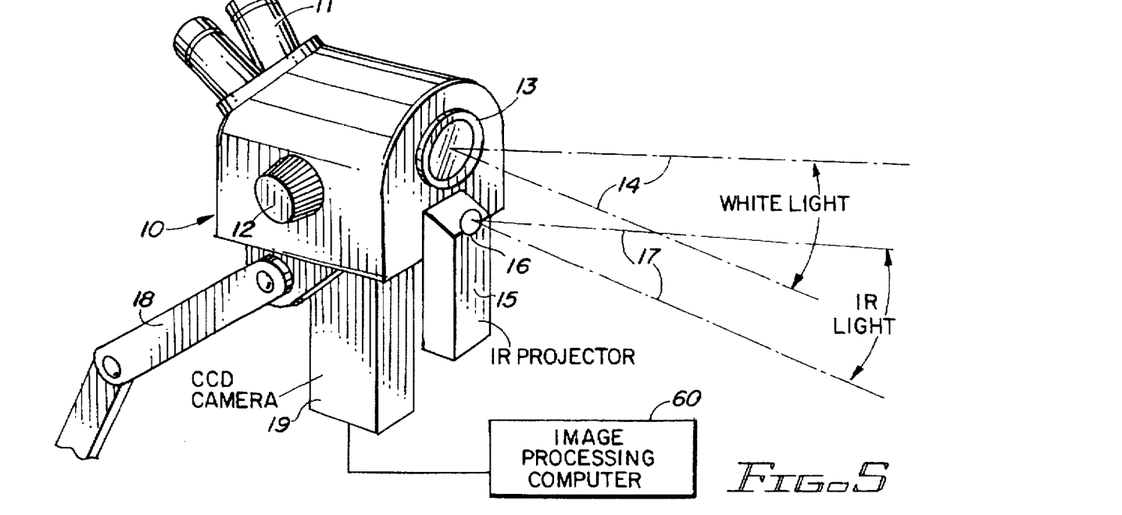
FIG. 5 is a partial perspective view of a colposcope of the present invention.

In FIG. 5, numeral 10 designates a digital imaging colposcope having a dual eyepiece 11, an image magnification control knob 12, an objective lens 13, and an articulated support arm 18. Digital image processing is made possible by the addition of a CCD camera 19, the digital output of which is coupled to an image processing computer 60. Colposcope 10 contains an internal illumination source that produces an illumination beam 14 of white light that illuminates the cervix being visualized. The above mentioned portion of the colposcope 10 is known.

The most common way of detecting cervical or vaginal cancer is to perform a pap smear on the patient in the gynecologist's office. The pap smear sample is sent to a laboratory for evaluation, usually after the patient goes home. If a positive result is obtained from the evaluation, the patient must return to the gynecologist's office. The gynecologist then uses a prior art colposcope to locate the site at which a biopsy is needed. The gynecologist takes the biopsy tissue sample and sends it to a laboratory for analysis, usually after the patient leaves. If necessary, the patient is advised to return for whatever surgical, chemical exfoliation, or freezing treatment is recommended.

The major problems with the foregoing prior art techniques are the high cost and the amount of time required for three patient visits, and the fact that many patients become fearful and fail to comply with the gynecologist's instructions to return for more analysis, surgery, etc. Furthermore, the absence of accurate information on the size and area of cervical lesions may result in some gynecologists being influenced in favor of surgical treatment of HPV lesions because of the substantial fee for this service.

There is a very clear and strong need for a technique that will allow a gynecologist to examine the cervix, determine if any known lesions have increased in area enough to warrant surgical treatment, and to determine if the lesions consist of pre-cancerous or cancerous tissue, all in the same patient visit. A technique for measuring the area of a lesion of the cervix should be easily incorporated into common examination procedures and should be compatible with variations in equipment (such as colposcopes) used by various physicians. The technique should be non-invasive, and the accuracy of lesion area measurements should be sufficient to reduce errors in the measurement to approximately those of an orthogonally viewed lesion. Furthermore, the elapsed time between the physician's examination of the patient and the availability of lesion area measurement results should be minimal, perhaps a few minutes.

The possibility of erroneous determinations of the progression of a cervical lesion has been of great concern to physicians for a number of years. However, despite the great need for a practical solution to this problem none has yet been proposed.

SUMMARY OF THE INVENTION

Accordingly, it is object of the invention to provide a technique which can be used to obtain correct area measurements on three-dimensional objects taken from two-dimensional images thereof.

It is another object of the invention to provide an improved colposcope and method which can economically provide accurate analysis of the size of a cervical lesion.

It is another object of the invention to provide an improved colposcope and method which allows inexpensive and accurate determination of changes in the size of a cervical lesion.

It is another object of the invention to provide a colposcope and method which overcomes the shortcomings of the closest prior art colposcopes and methods of using them.

It is another object of the invention to provide a practical technique for determining a reference cervix reflectance map of the human cervix.

It is another object of the invention to provide a practical technique for determining a reference body part reflectance map of a human body part.

It is another object of the invention to provide a practical technique which allows physicians to determine the reference reflectance map of a human body part, such as a cervix, which technique does not require that all physicians use the same imaging equipment.

It is another object of the invention to provide a practical technique that allows physicians to determine the actual area of a feature of a body part, such as a cervix, which does not require that all physicians use the same imaging equipment.

It is another object of the invention to provide a cervical reference reflectance map to allow for accurate measurement of areas of the surface of a human cervix observed using a colposcope.

It is another object of the invention to provide a technique for measuring areas on the surface of a human cervix in a non-invasive manner.

Briefly described, and in accordance with one embodiment thereof, the invention provides a technique for determining the area of a three-dimensional lesion on a cervix from a two-dimensional image thereof. A digital colposcope system is used for producing two-dimensional image coordinate data including intensity values at each pixel, respectively, of a two-dimensional image of the cervix. A standard reference reflectance map representing a reference cervix is stored in a computer. The standard reference reflectance map includes slant angles and corresponding gray scale intensity levels obtained in conjunction with a shape-assuming target including thereon an array of circular spots, the shape-assuming target assuming the shape of any cervix when placed thereon, and also in conjunction with a first stiff target having thereon a first circular spot of the first reflectivity and a second circular spot of a second reflectivity different than the first reflectivity. The first and second reflectivities define a gray scale range of the first stiff target. A second stiff target is placed on the cervix. The second stiff target has thereon a first circular spot of the first reflectivity and the second circular spot of the second reflectivity; the first and second reflectivities thereof define a gray scale range of the second stiff target. The digital colposcope system is operated to produce a first two-dimensional image of the lesion and the second stiff target. The intensity values of the first two-dimensional image are calibrated according to a relationship between the gray scale of the second stiff target and the gray scale of the first stiff target. The calibrated intensity values of the first two-dimensional image are correlated to the intensity values of the standard reference reflectance map to determine slant angles of the cervix at each pixel of the first two-dimensional image. A pixel dimension of each pixel in a portion of the first two-dimensional image including the lesion is corrected in accordance with the slant angle of the cervix at that pixel to obtain corrected three-dimensional pixel areas. The corrected three-dimensional pixel areas then are summed to obtain the three-dimensional lesion area.

DETAILED DESCRIPTION OF THE PREFERRED EMBODIMENTS

Obtaining a two-dimensional image of the cervix requires obtaining a measurement of the intensity of the image reflected from a corresponding area of the cervix at each pixel thereof. The local "slant angle" must be determined at each pixel of the two-dimensional image before corresponding three-dimensional information can be computed. The amount of light reflected from the cervix back to the objective lens of a colposcope and associated CCD camera depends primarily on the "slant angle" between the line perpendicular to the surface and the optical axis of the objective lens. In FIG. 1A, the slant angle σ is the angle between the direction 28 pointing from a lesion of area A directly to the lens of viewing colposcope and a "normal vector" 27 which is perpendicular to the lesion 25. "a" is the area projected (as indicated by projection lines 29) in the direction 28 by lesion 25 onto the lens of the colposcope, and is less than the actual area A of lesion 25.

Obtaining accurate area measurements of a three-dimensional object makes it necessary to have information, such as the slant angle, which represents the three-dimensional geometry of the target for each pixel of the image. The image intensity at each pixel is affected by how much illumination light is reflected back to the colposcope and its associated CCD camera to establish the intensity for each pixel. (The term "digital colposcope" is intended to encompass a system including a colposcope and a camera which produces digital data that represents its the image being viewed through the colposcope.) Some of the point source illumination light is reflected, some is absorbed by the cervix, and some of the light is scattered. The amount of illumination light that returns from the corresponding area of the cervix to the corresponding pixel of a CCD camera is affected by the nature of the reflecting surface. Note that the internal illumination source producing white light 14 in the colposcope 10 of FIG. 5 mentioned above, when used in conjunction with the present invention, must approximate a point light source in order for the technique of area correction described herein to work properly. (Use of a diffuse light source would invalidate the results obtained according to the technique described.)

Before describing the details of the presently preferred embodiments of the invention, it will be helpful to set forth the mathematical basis for the "correction" of computations of areas based on two-dimensional image data of a "sloped" surface of a three-dimensional object, such as a cervix. (It should be appreciated that the problem of obtaining a reflectance map of the cervix can not be solved by merely excising and then making measurements of reflective properties of such cervical tissue, because healthy living tissue has much different reflecting properties than dead tissue; specifically, the color, texture, and lubrication properties of living cervical tissue are much different than those of dead cervical tissue.)

The three-dimensional shape of the object has a direct effect on the way in which light reflects from the object. This is seen by an observer as differences in shading on the object. (For example, the effect referred to often is utilized by artists to give a three-dimensional impression in their two-dimensional artwork.) The image irradiance I(x,y) at a point on the surface of the object is a function of (1) the slant angle of the surface of the object at that point in relation to the optical axis along which the object is observed, (2) the intensity of the illuminating light, and (3) the physical characteristics of the object surface.

For the special case when the light source and viewer are oriented in the same direction relative to the object (which is the case when the cervix is viewed through a colposcope), the relationship of the object radiance (image irradiance) and the surface structure is simplified to:

$$E(x,y) = R(n(x,y)), \quad (1)$$

where E(x,y) is the "object radiance" at point x,y of the image, R(n(x,y)) is the "reflectance map" for the surface and "n" is the unit normal vector to the surface at the point (x,y) of the image. The reflectance map is a model that represents the amount of illumination reflected from the cervix as a function of the local slant angle. The reflectance map R(n)(x,y)) is a function of the physical characteristics of the surface which determine its reflectivity properties, and is proportional to the incident object irradiance $I_0$ that illuminates the object, as expressed in the following equation:

$$R(n) = I_0 r(n), \quad (2)$$

where r(n) is the reflectivity constant on the surface as a function of the surface normal direction. r(n) can be expressed as:

$$r(n) = m_1 \cos(\sigma) + m_2, \quad (3)$$

where σ is the slant angle of the surface relative to the viewer, and $m_1$ and $m_2$ are constants specific to the type of surface imaged.

A two-dimensional image of the object radiance E(x,y) is recorded through a colposcope using a CCD video camera such that each pixel of the image can be assigned a value which over some range is proportional to the object radiance E(x,y). All such video recording systems introduce an electronic gain and offset to the value corresponding to the image irradiance such that the pixel value measured is not the actual image irradiance, but is a linear transformation thereof and which can be expressed according to the equation:

$$I(x,y) = \theta E(x,y) + \beta, \quad (4)$$

where θ is the gain and β is the offset and I(x,y) is the object radiance as recorded by the imaging system accounting for the gain and offset of the imaging system. By substituting Equation 2 into Equation 1 and substituting for E(x,y) in Equation 4, the following equation can be obtained:

$$I(x,y) = \alpha r(n(x,y)) + \beta, \quad (5)$$

where α is the product of the object irradiance $I_0$ and gain θ. In this equation, α and β will vary from image to image, depending on the light intensity and the processes affecting the transformation of image irradiance at the camera into pixel values (such as different brand of camera, etc.). On the other hand, the reflectivity constant r(n) depends only on the reflecting properties of the object in the "scene" and the slant angle of the surface relative to the viewer.

By measuring values of object radiance I for two "standards" with two different reflectivity constant values $r_1$ and $r_2$ to obtain the values $I^{s1}$ and $I_{s2}$, respectively, under "standard reference" conditions (i.e., using the same imaging system and illumination intensity), it is possible to normalize the object radiance of any other "new" image to one standard reference if the standard target with the two different reflectivity constant values $r_1$ and $r_2$ is included in the field of view of the new image. Then, in accordance with the present invention, physicians can use various different imaging equipment, as long as each imaging system includes a copy of the standard in the image being measured. The foregoing can be shown to be true by considering the following group of equations.

For the reference image, $$I_{s1} = \alpha r_1 + \beta, \text{ and}$$

$$I_{s2} = \alpha r_2 + \beta,$$

and analogous equations are applicable to the "new image", except that the illumination intensity, gain and offset may be different, as indicated by the following equations:

$$I_{s1}' = \alpha' r_1 + \beta', \text{ and}$$

$$I_{s2}' = \alpha' r_2 + \beta'.$$

From the two foregoing equations, the following relationships can be derived:

$$\alpha' = \frac{(I_{s2}' - I_{s1}')}{(I_{s2} - I_{s1})} \alpha = A\alpha, \quad (6)$$

and $$\beta' = \frac{(I_{s2} I_{s1}' - I_{s1} I_{s2}')}{(I_{s2} - I_{s1})} + A\beta = B + A\beta. \quad (7)$$

In practice, the values of intensity for the two standards for the two values of $r_1$ and $r_2$ must be determined at all possible slant angles for which a correction may be desired. Therefore, the image to which all other images are to be referred must contain image information of a "reference object" including the two standard materials oriented at all possible slant angles. This image is referred to as the "standard reference image".

A new intensity I' (i.e., a new object radiance) of a pixel representing a present measurement of a particular patient's cervix is equal to:

$$\begin{aligned} I' &= \alpha' r_3 + \beta' \\ &= A\alpha r_3 + A\beta + B \\ &= A(\alpha r_3 + \beta) + B \\ &= AI + B, \end{aligned} \quad (8)$$

where I is the intensity that would have been observed in the reference image under the same conditions. Stated differently, the intensity I' is normalized to the intensity I of the standard reference image. The normalized value I' is easily transformed to that of the standard reference image by the equation:

$$I=(I'-B)/A. \quad (8a)$$

Therefore, for the conditions under which the standard reference image was obtained, the pixel intensity I has a value given by:

$$\begin{aligned} I &= \alpha r_3 + \beta \\ &= \alpha(m_1 \cos(\sigma) + m_2) + \beta \\ &= M_1 \cos(\sigma) + M_2, \end{aligned} \quad (9)$$

where $M1=\alpha m_1$ and $M2=\alpha m_2+\beta$.

Equation (9) is the "cervix reflectance model" of the patient's cervix. The "mean cervix reflectance model" representative of the cervixes of a population of n women is obtained by performing a linear least squares regression analysis using the corrected image intensity I as the independent variable, and the corresponding cosine of the angle (cosine $\sigma$) as the dependent variable determined from the population of women. This regression analysis allows the calculation of the best statistical estimator of the population value for $M_1$ (which is the slope of the regression line) and $M_2$ (which is the intercept of the regression line).

The relationship $M_1 \cos(\sigma)+M_2$ is referred to as the "reference reflectance map" of the reference object. The values of $M_1$ and $M_2$ vary, depending upon the properties of the surface of the object being observed. If the constants $M_1$ and $M_2$ are known, then the surface slant angle $\sigma$ can be determined as follows from the intensity of the background light recorded at that site on the surface of the object by rearrangement of Equation 9:

$$\sigma = \cos^{-1}\left(\frac{I-M_2}{M_1}\right). \quad (10)$$

The surface slant angle $\sigma$ provides sufficient information regarding the three dimensional structure of the object to allow for a correction of measurements over the area at which the angle is determined to correct for errors in the computation of that area based only on two-dimensional image data. The correction is simply the pixel dimension divided by cosine of the slant angle of that pixel.

In accordance with the present invention, a technique is provided for (1) determining the normalized reference cervix reflectance map of a reference cervix, (2) calculating corrected area measurements using the normalized reference cervix reflectance map and (3) computing a mean normalized reference cervix reflectance map which represents the human cervix for a population of women.

Figure 2A:
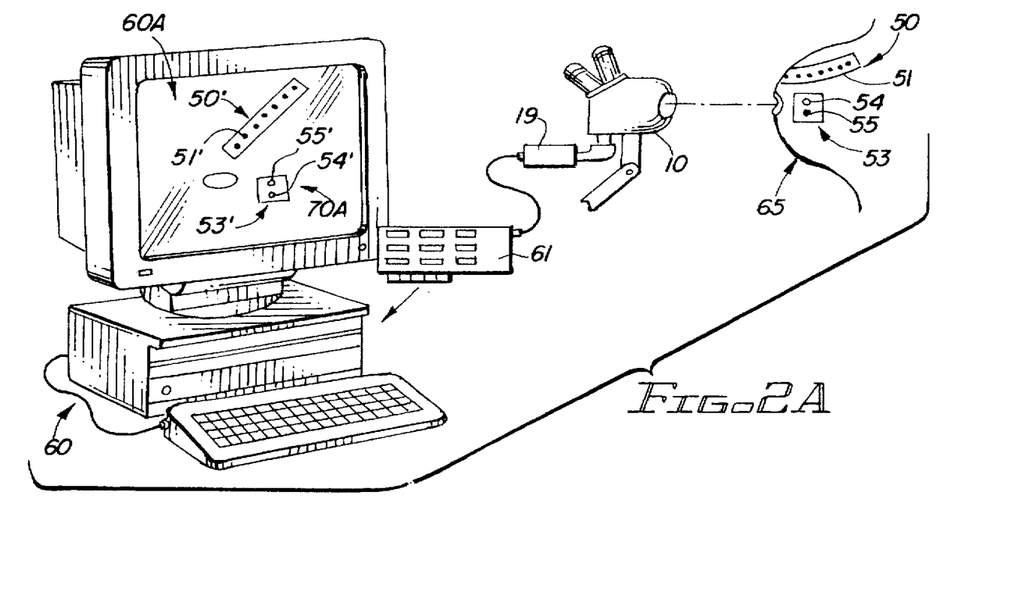
FIGS. 2A and 2B are partial perspective diagrams illustrating the apparatus of the invention and are useful in describing the structure and use of the invention in conjunction with both the shape-assuming target and stiff target of FIG. 1.

The presently preferred embodiments of the invention provide a technique for determining the "reference cervix reflectance map" of the human cervix 65 using the system shown in FIG. 2A.

After a suitable reference cervix reflectance map of the cervix has been determined, the cervix 65 of an individual patient is viewed through colposcope 10. The view of cervix 65 is recorded using a video camera 19 attached to the colposcope optics. The video signal from the camera is routed through computer 60, which makes measurements of area and brightness of the resulting image displayed on the computer monitor 60A using commercially or publicly available image processing software, such as "NIH IMAGE", which is available from the National Institutes of Health.

Figure 1:
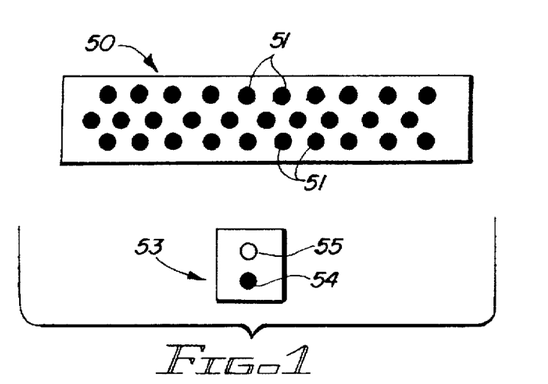
FIG. 1 is a plan view of a shape-assuming target with a predetermined pattern and a "standard" stiff target with a predetermined pattern thereon for use according to one embodiment of the invention.
Figures 1A, 6:
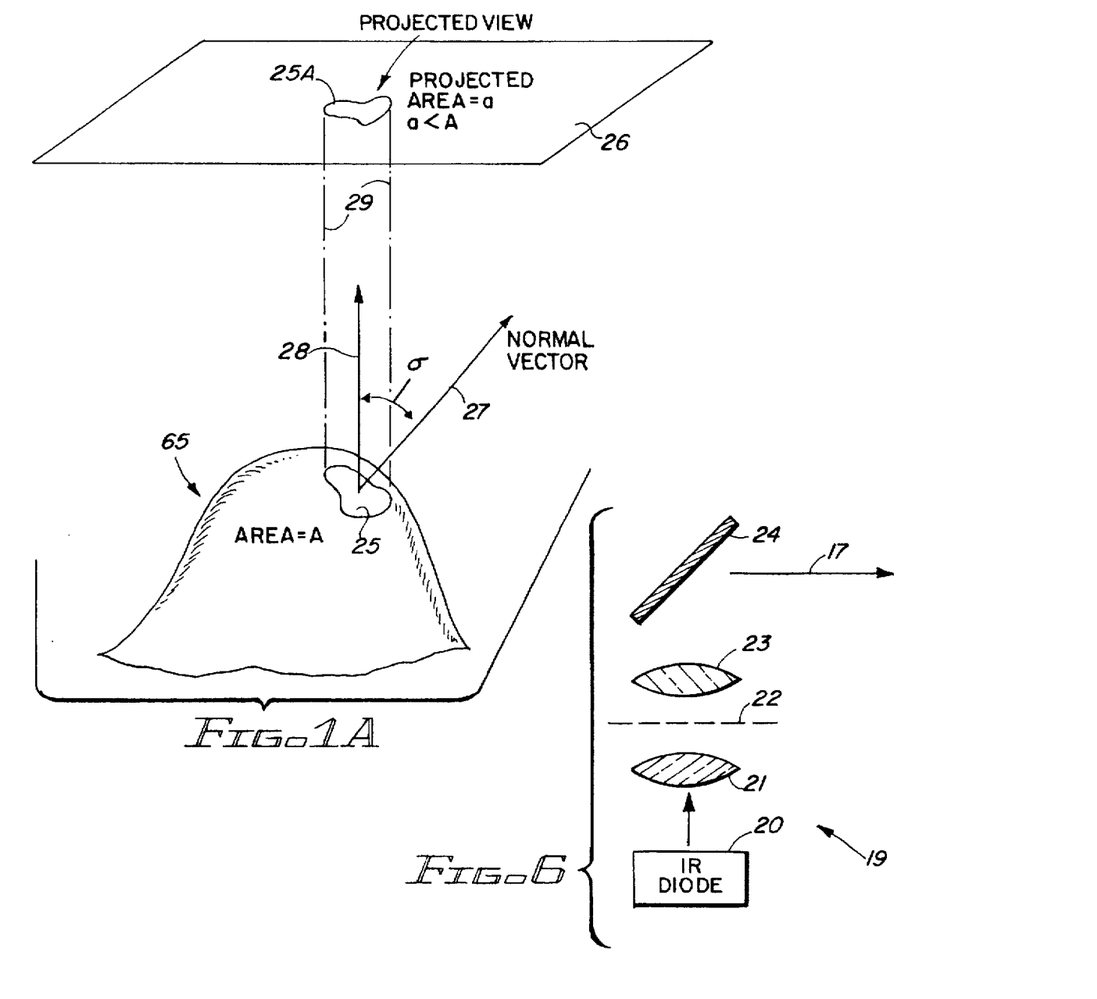
FIG. 1A is a diagram useful in explaining slant angle and its effects on intensity of light radiated from the cervix.
FIG. 6 is a schematic diagram of the arrangement of elements within the infrared projector 15 included in FIG. 5 in accordance with the present invention.
Figure 1B:
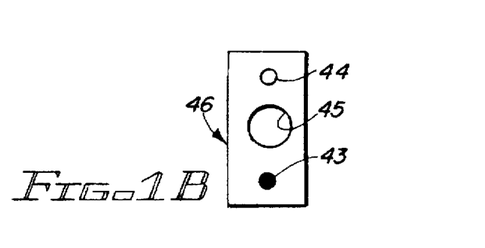
FIG. 1B is a diagram of a stiff target including a cutaway portion for exposing an underlying area of interest of a cervix.

To determine the reference cervix reflectance map, a shape-assuming target 50 of FIG. 1 is formed of a thin strip of paper having a number of imprinted round black dots 51 of 1 millimeter diameter. Shape-assuming target 50 is placed on cervix 65, whereupon it absorbs moisture from and adheres to cervix 65 and assumes the local surface configuration thereof. Shape-assuming target 50 can be composed of cellulose filter paper with the dark circular dots 51 imprinted thereon. The human cervix includes mucosa which wet the cellulose filter paper immediately, causing it to absorb the mucosa almost immediately and adhere almost perfectly to the contour of the cervix.

A stiff paper "standard target" 53 with a 1.5 millimeter diameter dark dot 54 and a 1.5 millimeter light dot 55 also is placed on cervix 65. Each of the dots 54 and 55 on standard target 53 has a corresponding reflectance which is known as a function of slant angle $\sigma$. Since standard target 53 is stiff, it does not take on the local surface shape of cervix 65 but instead defines a planar surface at a particular angle to the viewing angle or optical axis of the colposcope.

A digital first image then is captured for analysis from the CCD camera 19 (FIG. 5) associated with colposcope 10 in digital format by a conventional frame grabber board 61 in computer 60. Shape-assuming target 50 then is removed from cervix 65, and a digital second image of the same spot on cervix 65 is immediately captured by colposcope 10, CCD camera 19, and frame grabber 61. The first and second images are identical except that the first image includes an image of shape-assuming target 50 and its dots 51, and the second image includes an image of the tissue of cervix 65 that was under the shape-assuming target 50. Both the first and second images include the stiff gray scale calibrating target 53.

Dots 51 of shape-assuming target 50 of the first image (of shape-assuming targets 50) appear as circles 51' on computer monitor 60A whether the slant angle is 90 degrees with respect to the viewer. Wherever the slant angle is not 90 degrees, circular dots 51 of target 50 appear as ellipses 51' on computer monitor 60A. The cosine of the local slant angle $\sigma$ can be calculated from the ratio of the minor axis "a" to the major axis "b" of the apparent ellipses 51' according to the following expression:

$$\cos(\sigma)=a/b, \quad (11)$$

where "a" is the minor axis of the subject ellipse 51' and "b" is the major axis of that ellipse. This permits determination of the slant angle $\sigma$ of cervix 65 at each location where there was a circular dot 51 on shape-assuming target 50, and thereby provides the three-dimensional information necessary to obtain the total area of the three-dimensional lesion from the two-dimensional intensity data produced by the CCD camera.

The "background intensity" of the second image (of the tissue of cervix 65) can be determined in the same x,y locations corresponding to the x,y locations of ellipses 51' in the first image (of shape-assuming target 50). The slant angle and image radiance at specific Cartesian coordinates (x,y) in the second image (of cervix 65) thus are known.

Figure 3:
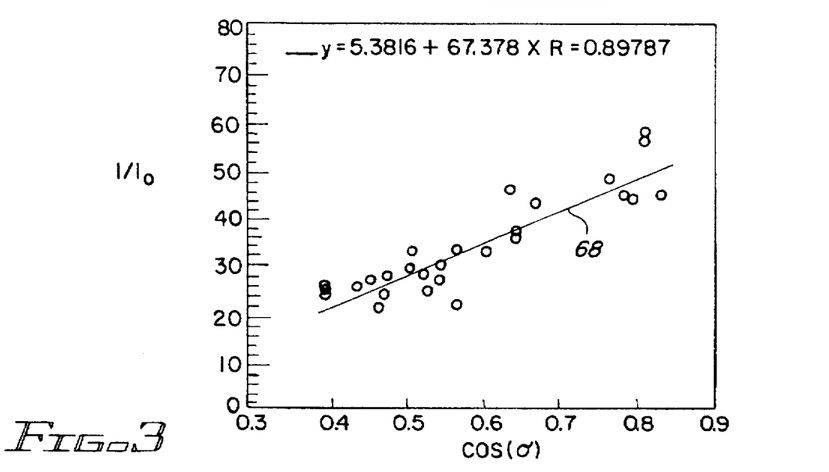
FIG. 3 is an illustration of a reflectance map diagram for an individual human cervix.

The background intensity then is determined by fitting a high order polynomial to a line passing through the x,y coordinates in the second image (of cervical tissue) corresponding to the centers of the dots on shape-assuming target 50 in the first image, as shown in FIG. 3, using pixels that do not correspond to "high spatial frequency" features (such as blood vessels) of cervix 65. This results in a "first set of matched data points" $\cos(\sigma)_i, I_i'$ for i=1,2,3 ... n, where n is the number of dots 51 on shape-assuming target 50.

The stiff standard target 53 in the second image (of cervical tissue previously under shape-assuming target 50) is analyzed by determining the apparent major axis and minor axis for the image of each dot on the standard target 53, and the average gray level intensity of each such dot is determined. The cosine of the slant angle σ of stiff standard target 53 is obtained from the ratio of the minor/major axes a and b of the image ellipses 54' and 55' appearing on monitor screen 60A. The average intensities of the pixels of the image ellipses 54' and 55' are assigned the values $I_{a1}'$ and $I_{a2}'$. The values of $I_{s1}$ and $I_{s2}$ from the standard reference image at the slant angle σ corresponding to the slant angle of stiff standard target 53 are then used to calculate the correction factors A and B as:

$$A = \frac{(I_{s2}' - I_{s1}')}{(I_{s2} - I_{s1})} \quad (12)$$

$$B = \frac{(I_{s2}I_{s1}' - I_{s1}I_{s2}')}{(I_{s2} - I_{s1})} \quad (13)$$

In the intensity measurements of the first set of matched data points $(\cos(\sigma)_i, I_i')$, $I_i'$ is replaced by $I_i$ where $I_i=(I_i'-B)/A$ to provide a "second set of matched data points" $(\cos(\sigma)_i, I_i)$ that are normalized. The second set of matched data points is then plotted with $I_i$ being the dependent variable. A least squares analysis can determine the statistically best value for $M_1$ as the slope of the plotted data and $M_2$ as the intercept of the linear plot.

Such measurements (first and second sets of data) were obtained for a population of n=50 women, and the "mean reference cervix reflectance map" of a "reference cervix" was calculated from such measurements. (The term "reference cervix" is intended to encompass both one cervix used as a typical reference or a hypothetical cervix having an "averaged" slope and "averaged" reflective properties.) The mean reference cervix reflectance map of the normal human cervix for one population of 50 women was found to be:

$$I = M_1 (\cos(\sigma)) + M_2, \quad (14)$$

where $M_1 = 70$ $M_2 = -6$.

Even though the reflectance of the cervix is not a function of the imaging system used, $M_1$ and $M_2$ can be different for various imaging systems. For a particular configuration of colposcope and camera, the mean reference cervix reflectance map for one population of women was found to have approximately the above values. Of course, different values of these numbers $M_1$ and $M_2$ would be obtained for other specific configurations of imaging equipment using the present technique.

The mean reference cervix reflectance map can be used to correct the pixel dimensions of the area of the image that is selected for measurement by providing the cosine of the slant angle of that pixel. The cosine of the slant angle σ is determined by simple rearrangement of Equation 6 as follows:

$$\cos(\sigma) = (I - M_2)/M_1 \quad (15)$$

so that the corrected pixel dimension is corrected pixel dimension=pixel dimension/$\cos(\sigma)$ (16)

The area is determined by selecting those n pixels in the image that correspond to the area of interest and forming a "third set of matched data points", of length n, of the background light intensity of the pixels. The corrected area $A_c$ then becomes:

$$A_c = \sum_{i=1}^{n} (mm^2/\text{pixel})/((I_1 - M_2)/M_1) \quad (17)$$

Next, the use of the above principles in the preferred embodiment of the invention will be explained. The "standard target reflectance map" need only be prepared once, and thereafter can be used to standardize or "normalize" all subsequent images of cervical tissue.

This standard target reflectance map is prepared by imaging rows of dots 54 and dots 55 which are placed around a cylinder (not shown) to provide a range of slant angles $\sigma_i$ to camera 19 from 0° to 90°. The cosines of the angles can be determined by the ratios of the minor axes "a" to the major axes "b" of the resulting imaged ellipses. A plot of the gray level intensities measured by CCD camera 19 for the various dots 54 and the various dots 55 versus the slant angles of such dots allows the determination of a linear relationship between the gray levels and the slant angles $\sigma_i$. In this way, the values of $I_{s1}$ and $I_{s2}$ for the corresponding slant angles in the new image can be determined.

The "reference cervix reflectance map" of a reference cervix is determined by placing shape-assuming target 50 constructed of a thin paper which contains the black circular targets of known dimension onto cervix 65. The paper absorbs moisture from cervix 65, adheres closely to it, and assumes the local surface shape thereof. FIG. 1 shows a diagrammatic representation of the shape-assuming target 50, and also of standard calibration target 53, which is constructed of stiff paper containing the standard dots 54 and 55, each with a measured reflectance map of its own, is also placed on cervix 65 near shape-assuming target 50 as shown in FIG. 2A. FIG. 1 also shows a diagrammatic representation of calibration target 53 which is also referred to as "standard target" 53.

Colposcope 10 with attached video camera 19 is used to observe the circular dots 51 of shape-assuming target 50 and the circular dots 54 and 55 of calibration target 53. The video image signal is routed through computer 60 equipped with frame grabber board 61 which allows a 256 bit gray level digital image of the view to be captured, resulting in an image 70A on monitor 60A in FIG. 2A.

Figure 2B:
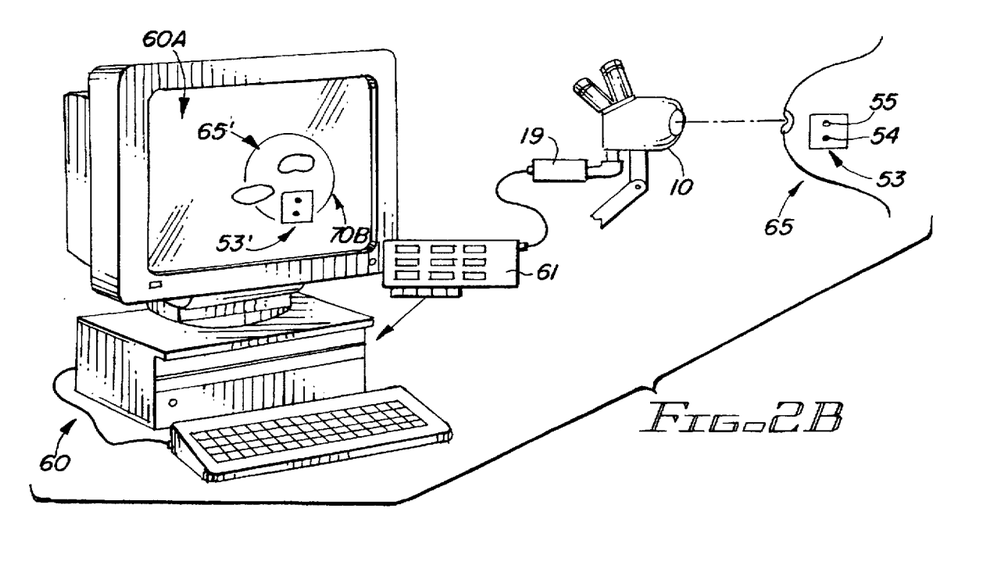

Without moving cervix 65 or colposcope 10, shape-assuming target 50 is removed from cervix 65 and the resulting colposcope view of cervix 65 without shape-assuming target 50 is immediately captured by computer 60, resulting in an image 70B as shown in FIG. 2B. Images 70A and 70B differ only by the presence of shape-assuming target 50 in image 70A.

The local surface angle σ of a cervix with respect to the view of colposcope 10 is determined at each region of cervix 65 where the circular targets 51' are positioned in image 70A (FIG. 2A) due to the geometrical effect wherein the "apparent shape" of a circle in a plane with a non-zero slant angle appears in a two-dimensional image as an ellipse. The cosine of the surface slant angle σ is calculated according to Equation 11 as the ratio of the minor to major ellipse axes. The lengths of the major and minor axes of each elliptical target image 51' on computer monitor 60A which can be automatically measured by counting the number of pixels that make up each of the major and minor axes, respectively, and the inverse cosine of the ratio of the minor to major axes is determined to provide the slant angle σ at that point.

At locations in image 70B of FIG. 2B corresponding to the same locations of circular targets in image 70A of FIG. 2A, the background reflected light intensity of cervical tissue is determined by fitting a third degree polynomial equation to the background gray level intensity, excluding regions containing features such as blood vessels or specular reflection, and determining the gray level value from the polynomial equations of the pixels in image 70B that have the same coordinates as the targets of image 70A. This results in the above "first set of matched data points" of reflectance light intensities, $I_i'$, with corresponding values for the cosines of the slant angles, i.e., $\cos(\sigma)i$ for i=1,2,3 . . . n, where n is the number of dots 51 on shape-assuming target 50.

The values of A and B for normalizing the image intensities to corresponding intensities of the standard target reflectance image are determined by first measuring the average gray level of images of two dots 54 and 55 on computer monitor 60A to provide $I^{s1'}$ and $I_{s2}'$, respectively. The cosine of the angle of the dots 54 and 55 on standard target 53, $\cos(\sigma_s')$, is determined by the ratio of the minor axes "a" to major axes "b" of the images of dots 54 and 55. The values of $I_{s1}$ and $I_{s2}$ at the same $\cos(\sigma_s')$ are already known from the standard target image. Therefore, the normalizing constants A and B are calculated according to Equations 12 and 13:

$$A = \frac{(I_{s2}' - I_{s1}')}{(I_{s2} - I_{s1})}$$

and $$B = \frac{(I_{s2}I_{s1}' - I_{s1}I_{s2}')}{(I_{s2} - I_{s1})}$$

The reflectance light intensities of the above mentioned "first set of matched data points" are then normalized by substituting $(I_i'-B)/A$ for $I_i$ producing the above mentioned "second set of matched data points" including matched pairs of $\cos(\sigma)_i$ and normalized intensities $I_i$.

The reference cervix reflectance map constants M1 and M2 are determined by a linear least squares regression analysis of the intensities and cosines of the slant angles σ in the second set of matched data points with $M_1$ being the slope of the line and $M_2$ being the intercept. FIG. 3 shows a graph of a plot of the intensity versus the slant angle for one example of the second set of matched data points with the calculation of the "linear least squares best fit" to the second set of matched data points. The determination of these constants completes the description of the "normalized" reference cervix reflectance map of cervix 65, which constitutes or represents a stored mathematical model of the cervix.

The correction of area measurements obtained from image 70B of FIG. 2B is accomplished by first identifying those pixels of the image that are included in the lesion area being measured. This is typically done by using a pointing device, such as a computer mouse, to move a cursor on monitor 60A so as to outline the lesion area to be measured. This results in selection of m pixels. This provides the above mentioned "third set of matched data points" of $(x_i, y_i, I_i')$ with i=1,2,3 . . . n, where $x_i, y_i$ are the Cartesian coordinates and $I_i'$ is the gray level value or intensity of that pixel. The values for $I_i'$ in the third matched data list are replaced with "normalized" intensity values $I_i$ where $I_i$ is equal to $(I_i'-B)/A$ according to Equation 8. The cosine of the slant angle σ for each pixel is then determined using $I_i$ according to Equation 15, where $I_i$ is substituted for I. This $(\cos(\sigma))_i$ is added to the third set of matched data points, which is equal in length to n, the number of pixels selected to represent the area in question. The corrected area $A_c$, of the cervix is then determined using the following equivalent of Equation 9 and the cosine angles in the third set of matched data points:

$$A_c = \sum_{i=1}^{n} (mm^2/\text{pixel})/(\cos(\sigma)_k),$$

Since the above description is rather complex, it will be helpful to provide the following summary of the foregoing procedure.

TO SUMMARIZE

I. To Prepare a "Standard Target Reflectance Map":

1. Wrap a strip of Reflectivity 1 ($r_1$) material and a strip of Reflectivity 2 ($r_2$) material around a cylinder.

2. Using the digital colposcope 10 and a particular point light source, take an image of the cylinder and the two strips thereon to form a "Standard Image". (The gray level intensities of subsequent images taken for a reference cervix and a patient's cervix must be "normalized" to this Standard Image.)

3. Measure the gray level intensities of the Reflectivity 1 strip and the Reflectivity 2 strip at a number of angles from 0 to 90 degrees to thereby produce the "Standard Target Reflectance Map" for each of the Reflectivity 1 strip and the Reflectivity 2 strip. The gray level intensity for each strip will be a function of the cosine of the slant angle.

II. To Prepare a "Normalized Reference Cervix Reflectance Map":

1. Place a shape-assuming target 50 on a reference cervix.

2. Place a standard target 53 on the reference cervix.

3. Using the same or equivalent colposcope and point light source, make "Image 1" of shape-assuming target 50 and standard target 53 on the reference cervix.

4. Remove shape-assuming target 53 and immediately make "Image 2" of the reference cervix tissue immediately under target 50 and the standard target 53.

5. Normalize the gray level intensity of Image 2 using the intensity of the Reflectivity 1 dot (55), the intensity of the Reflectivity 2 dot (54), and the Standard Target Reflectance Map.

6. Produce the Normalized Reference Cervix Reflectance Map by determining from Image 1 the eccentricity ratios and hence the slant angles of each of the circular dots 51, respectively, of the shape-assuming target 50, and correlate the normalized intensities of the pixels of the cervix in Image 2 with the slant angles of the circular dots 51 (Image 1) including those pixels, respectively.

7. If desired, repeat steps 1–6 for a number of reference cervixes and combine the results to provide a "Mean Normalized Reference Cervix Reflectance Map".

III. To Measure the Area of a Lesion of a Patient's Cervix:

1. Place a standard target 53 on the patient's cervix near (i.e., included in the same digital image as) the lesion 25.

2. Produce a digital image using the same or equivalent equipment used to prepare the Standard Target Reflectance Map and the Normalized Reference Cervix Reflectance Map to produce a digital image of the lesion 25 and standard target 53.

3. Normalize the gray level intensities of the digital image using the measured pixel intensities of the Reflectivity 1 dot (55), Reflectivity 2 dot (54) of standard target 53, and the Standard Target Reflectance Map.

4. Determine the slant angles at pixels of the patient's cervix containing the lesion 25 by correlating the normalized intensity values determined in foregoing Step 3 with the normalized intensities of the Normalized Reference Cervix Reflectance Map, thus obtaining the slant angles corresponding thereto.

5. Correct the pixel dimensions of each pixel of the image of the lesion in accordance with the slant angle of the lesion at that pixel as determined in foregoing Step 4 to obtain corrected three-dimensional pixel areas.

6. Sum the corrected three-dimensional pixel areas to obtain the three-dimensional area of the lesion.

Figure 4:
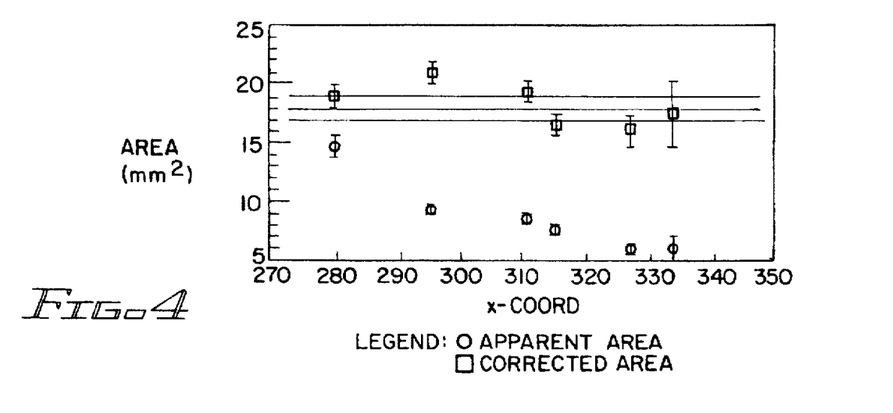
FIG. 4 is a diagram illustrating correction of area measurement as a function of distance from the area being measured from the cervical os.

The graph of FIG. 4 illustrates several "uncorrected" lesion areas and corresponding lesion areas corrected according to the present invention.

It is well known that projection of a grid pattern on a three-dimensional object causes distortion of the grid pattern from its actual two-dimensional appearance. In some cases, the three-dimensional coordinates x,y,z of the object surface can be constructed from the differences between the imaged grid pattern returned by the three-dimensional object (i.e., the cervix) and stored data representing the two-dimensional configuration of the grid. FIG. 5 shows an alternate colposcope 10 and CCD camera 19 coupled to an image processing computer 60 which is based on the foregoing technique. Image processing computer 60 stores an accurate image of grid 22, and also receives the projected grid pattern as it is distorted by the cervix and imaged back into colposcope 10.

A suitable mathematical model representative of an idealized cervix can be stored in image processing computer 60. Image processing computer 60 processes two-dimensional digital image data by executing any of a number of commercially available image processing programs to obtain a three-dimensional profile of the cervix. The differences between the projected grid pattern and the grid pattern "distorted" by the cervix and transmitted therefrom back into colposcope 10 and digitally imaged by CCD camera 19 and image processing computer 60 and the stored three-dimensional model of an ideal cervix are computed. Such differences are used to mathematically construct a three-dimensional profile of the cervix being presently visualized. It then is a simple matter to accurately compute the surface area of any imaged feature, such as an HPV lesion, from the mathematical model of the actual cervix being imaged. It should be appreciated that the compound curvature of the cervix also complicates any technique based on projecting of geometrical pattern, for example, an array of circles, on the cervix and then measuring the distortion that appears in the two-dimensional image thereof and processing that information to obtain three-dimensional information representing the surface of the cervix. However, the computer program and mathematics for computing three dimensional image information from such data is far more complex and time consuming to calculate than for the embodiment of the invention described with reference to FIGS. 1–4.

Note that a common theme between the embodiments of the invention described with reference to FIGS. 1–4 and 5 is that both involve stored mathematical models of the human cervix which are used to compute the area of three-dimensional features from two-dimensional image intensity data obtained from the cervix, on the basis of which accurate computations of the area of lesions on sloped surfaces of the cervix are computed and compared with corresponding previous computations of the area of the same lesion to determine if there has been a significant change thereof.

In any case, by taking such digital colposcopic images of a woman's cervix at selected time intervals (for example every three months), a precise determination of the amount of growth or shrinkage of an HPV lesion can be accurately determined. The gynecologist then can use such information to make well founded decisions as to whether surgery or other treatment is required.

One concern in imaging a human cervix is that white areas of the epithelium frequently occur and result in too much image contrast. Generally, a smooth, "low frequency" distribution of the reflected light is most desirable, and this can be accomplished by limiting the spectral content of the image light received by the CCD camera, either by controlling the light source illuminating the cervix or by inserting an optical filter in front of the CCD camera to confine the spectral bandwidth of light reflected from the cervix to produce the image. Light in the optical infrared spectrum results in reducing image contrast.

The colposcope 10 of FIG. 5 also includes an infrared light projector 15 is attached to the above-described colposcope 10, and projects an infrared light beam 17. The axis of infrared light beam 17 and the axis of a white light beam 14 produced by objective lens 13 of colposcope 10 converge on the cervix at a distance of about 30 centimeters from objective lens 13 of colposcope 10 and lens 16 of infrared projector 15. The reflected white light image of the cervix returns to objective lens 13 and can be selectively directed into the objective lens (not shown) of CCD camera 19 and/or to the eyepiece 11.

FIG. 6 shows an arrangement of elements inside infrared projector 15, including an infrared diode 20, a condenser lens 21, a grid 22, a projection lens 23, and an inclined mirror 24. The projection lens pattern is a grid pattern as indicated by numeral 22 in FIG. 3, so that an infrared light grid pattern 17 having the appearance of grid 22 is projected onto the three-dimensional cervix and any HPV lesions thereon.

Use of infrared light outside of the visible range to project the rectangular grid onto the cervix while it is simultaneously illuminated by white light permits the physician to visually observe the cervix during an examination while the distorted infrared grid pattern reflected back to the colposcope and infrared camera is being digitized and analyzed by computer 60 so that a 3-D image can be computed and displayed on a monitor.

In some cases, a suitable reference cervix reflectance map may not be available for use with a particular patient. If a physician wishes to accurately profile a large portion of the cervix of such a patient, the physician may need to go through the time consuming process of creating a unique reference cervix reflectance map for that particular patient in order to use the above described technique of the present invention. Alternatively, the physician may quickly obtain an approximate reference cervix reflectance map through the use of two or more of the modified stiff targets 46 shown in FIG. 1A. Stiff target 46 includes a circular cutout 45 in addition to a dark circular dot 43 and a light circular dot 44. The physician can place two or more stiff targets 46 directly on the cervix with the only constraint being that they are within the field of view. Stiff target 46 will have a slant angle that corresponds to the slant angle of the area of the cervix exposed through cutout 46. The physician can use the digital colposcope 10 to image stiff target 45, including circular dots 43 and 44 and also the area of the cervix exposed through circular cutout 45. As explained above, the circular dots 43 and 44, and also the circular cutout 45, will be projected as ellipses onto the image plane of colposcope 10, and ratios between the minor axes and major axes of the respective ellipses will represent the slant angle of stiff target 46, and hence also of the area of the cervix exposed through cutout 45.

The colposcope 10 and computer 60 are operated to make useful intensity measurements of the exposed area of the cervix. This results in at least two intensity measures as a function of known slant angles. The two points are sufficient to define a line which approximates the reference cervix reflectance map of the cervix being observed. This reference cervix reflectance map may then be used to allow for the correction of area measurements as described above. The area of the feature of interest then can be used, for example, as baseline information for that patient and compared later with a similar area measurement to determine if there has been a significant change in size of the feature.

The above described embodiments of the invention, by providing fast, accurate determinations of the areas of lesions, accurate to approximately the accuracy of an orthogonally viewed lesion avoid the problems caused by the inability to accurately determine the areas of lesions of the cervix. The embodiment of FIGS. 1–4 provides the advantage of direct determination of the reflective map of a normal, living tissue cervix (or other internal body part) in situ. That embodiment of the invention also provides a mean reflectance map which functions as a mathematical model that accurately represents the cervix of a large population of women, and therefore is very useful for clinical use. The invention also allows researchers to easily create individual reflectance maps for each patient. As previously indicated, the invention can be used in conjunction with a variety of different imaging systems.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

For example, the same basic technique can be used for in situ determination or measurement of three-dimensional information on internal living tissue other than the cervix. For example, in the field of endoscopic surgery details of the geometry of the surface of such a body part often would be very desirable, especially if displayed in a real time on a video monitor. Such details could be obtained in accordance with the present invention by using an optical imaging device other than a colposcope. (Note that-the term "optical" as used herein is intended to include use of portions of the electromagnetic spectrum outside of the range of ordinary human vision.) Providing such images on the video monitor would require development of a reflectance map similar to the one described above.

Furthermore, the techniques of the present invention can be easily extended to accomplish three-dimensional mapping of the cervix or other tissue. The z coordinates of all pixels of the image can be computed if the pixel size and slant angle of each pixel are known. A perceived high point or low point pixel of the object can be selected as a three-dimensional reference point. Since the two-dimensional size of each pixel is known and the x and y coordinate values also are known for each pixel, then the z coordinate of the center point of each pixel relative to an adjacent pixel can be easily computed. This process can be performed repetitively in the x and y directions to successfully compute values of z for each pixel. The technique of the present invention can, of course, be used in conjunction with two-dimensional image equipment other than a colpascope. For example, a still digital camera or a standard photographic camera can be used in conjunction with a suitable point white light source.

The above-described embodiments of the invention can be further extended to two dimensional imagery obtained by other than direct digital means. For example, the original source images can be exposed on photographic emulsions, with the calibration targets positioned exactly as previously described. The photographic images are then digitized by any of a variety of digital imaging techniques (e.g. spot scanning, line scanning or two dimensional array imaging) and subsequently processed exactly as described previously for the direct digital images. It should be noted that the scene illumination requirements are similar to those for direct digital imaging, i.e., the use of a point, or near-point, source of light is critical; also, the reflection map is a function of the sensitivity of the detector. Thus, the logarithmic response of the typical photographic emulsion will result in a correction curve different in detail from the curve obtained for a linear silicon imager response. Nonetheless, the basic concept of area correction by application of reflection map data to the two dimensional image remains the same.

What is claimed is:

1. A method of determining the area of a three-dimensional feature on a body part from a two-dimensional image thereof, comprising the steps of:

(a) providing an imaging system for producing two-dimensional image coordinate data including intensity values at each pixel, respectively, of a two-dimensional image of a body part;

(b) storing a normalized reference body part reflectance map representing a reference body part, the normalized reference body part reflectance map including slant angles corresponding to gray scale intensity levels, respectively, the normalized reference body part reflectance map being normalized with respect to a predetermined standard reflectance map;

(c) placing a stiff target on the body part in a field of view including a three-dimensional feature, the stiff target having thereon a first spot of a first reflectivity and a second spot of the second reflectivity;

(d) operating the imaging system to produce a two-dimensional image of the feature and the stiff target;

(e) using intensity values and aspect ratio values of the first and second spots of the two-dimensional image to normalize intensity values of the two-dimensional image with respect to the predetermined standard reflectance map;

(f) correlating the normalized intensity values of the two-dimensional image to the normalized intensity values of the normalized reference body part reflectance map to determine slant angles of the body part at pixels of the two-dimensional image;

(g) correcting a pixel dimension of each pixel in a portion of the two-dimensional image including the feature in accordance with the slant angle of the body part at that pixel to obtain corrected three-dimensional pixel areas; and (h) summing the corrected three-dimensional pixel areas to obtain the three-dimensional feature area.

2. A method of determining the area of a three-dimensional lesion on a cervix from a two-dimensional image thereof, comprising the steps of:

(a) providing a digital colposcope system for producing two-dimensional image coordinate data including intensity values at each pixel, respectively, of a two-dimensional image of a cervix;

(b) storing a normalized reference cervix reflectance map representing a reference cervix, the normalized reference cervix reflectance map including slant angles corresponding to gray scale intensity levels, respectively, the normalized reference cervix reflectance map being normalized with respect to a predetermined standard reflectance map;

(c) placing a stiff target on the cervix in a field of view including a lesion, the stiff target having thereon a first circular spot of the first reflectivity and a second circular spot of a second reflectivity;

(d) operating the digital colposcope system to produce a two-dimensional image of the lesion and the stiff target;

(e) using intensity values and aspect ratio values of the first and second spots of the two-dimensional image to normalize intensity values of the two-dimensional image with respect to the predetermined standard reflectance map;

(f) correlating the normalized intensity values of the two-dimensional image to the normalized intensity values of the normalized reference cervix reflectance map to determine slant angles of the body part at pixels of the two-dimensional image;

(g) correcting a pixel dimension of each pixel in a portion of the two-dimensional image including the lesion in accordance with the slant angle of a body part at that pixel to obtain corrected three-dimensional pixel areas; and (h) summing the corrected three-dimensional pixel areas to obtain the three-dimensional feature area.

3. A method of determining the area of a three-dimensional lesion on a cervix from a two-dimensional image thereof, comprising the steps of:

(a) providing a digital colposcope system for producing two-dimensional image coordinate data including intensity values at each pixel, respectively, of a two-dimensional image of a cervix;

(b) storing a normalized reference cervix reflectance map representing a reference cervix, the reference cervix reflectance map including slant angles corresponding to gray scale intensity levels of images of the cervix that i. have been previously obtained in conjunction with an image of a shape-assuming target including thereon an array of circular spots placed upon the surface of the cervix and assuming the shape of any cervix when placed thereon, and an image of a first stiff target having thereon a first circular spot of the first reflectivity and a second circular spot of a second reflectivity different than the first reflectivity, and ii. have been normalized to a standard target reflectance map including slant angles corresponding to gray scale intensity levels of an image of the first and second reflectivities at a range of angles from 0 to 90 degrees obtained at illumination condition;

(c) placing a second stiff target on the cervix proximate to the lesions the second stiff target having thereon a first circular spot of the first reflectivity and a second circular spot of the second reflectivity;

(d) operating the digital colposcope system to produce a two-dimensional image of the lesion and the second stiff target;

(e) using intensity values and aspect ratio values of the first and second spots of the two-dimensional image to normalize the gray level intensities of the two-dimensional image of the lesion with respect to the predetermined standard target reflectance map;

(f) correlating the normalized intensity values of the two-dimensional image to the normalized intensity values of the normalized reference cervix reflectance map to determine slant angles of the cervix at predetermined pixels of the two-dimensional image;

(g) correcting a pixel dimension of each pixel in a portion of the two-dimensional image including the lesion in accordance with the slant angle of the cervix at that pixel to obtain corrected three-dimensional pixel areas; and (h) summing the corrected three-dimensional pixel areas to obtain the three-dimensional lesion area.

4. The method of claim 3 wherein the circular spots are all of equal size, and the first circular spot being dark and of low reflectivity, the second circular spot being light and of high reflectivity.

5. The method of claim 3 including performing steps (e), (f), (g) and (h) by executing an operating program in a computer.

6. The method of claim 5 including operating the computer to display the image of the lesion and to determine which pixels are therein by outlining the image of the lesion with a cursor before performing step (f).

7. The method of claim 3 including obtaining the standard target reflectance target map by performing the steps of i. imaging the circular spots on a plurality of stiff targets each having thereon a circular spot of the first reflectivity and a circular spot of the second reflectivity arranged-around a portion of a circumference of a cylinder;

ii. determining the cosines of the slant angles of the circular spots, respectively, by measuring the lengths of and obtaining the ratio of the minor axis and major axis of each imaged circular spot; and iii. measuring a gray scale intensity for each of the circular spots of the stiff target on the cylinder and correlating each gray scale intensity to a corresponding slant angle of that circular spot to thereby obtain a table of gray scale intensities and corresponding slant angles.

8. The method of claim 3 including obtaining the normalized reference cervix reflectance map by optically filtering light producing one or more cervix images from which an image of the reference cervix is obtained to spectrally narrow a band of light producing the one or more cervix images.

9. The method of claim 3 including obtaining the normalized reference cervix reflectance map by digitally filtering data representing one or more cervix images from which an image of the reference cervix is obtained to, in effect, spectrally narrow a band of light producing the one or more cervix images.

10. The method of claim 3 wherein step (b) includes using cellulose material as the shape-assuming target.

11. The method of claim 3 including using material from the group consisting of plastic, glass, paper, cellophane, and rubber as the first and second stiff targets.

12. The method of claim 3 wherein step (b) includes obtaining the normalized reference cervix reflectance map as a mean normalized reference cervix reflectance map by making intensity measurements of cervixes of a population of women.

13. The method of claim 3 wherein step (c) includes using a target identical to the first stiff target as the second stiff target.

14. A system for determining the area of a three-dimensional feature on a body part from a two-dimensional image thereof, comprising in combination:

(a) a computer;

(b) an imaging system for producing two-dimensional image coordinate data including intensity values at each pixel, respectively, of a two-dimensional image of a body part;

(c) a normalized reference body part reflectance map stored in a memory of the computer and representing a reference body part, the normalized reference body part reflectance map including slant angles corresponding to gray scale intensity levels, respectively, the normalized reference body part reflectance map being normalized with respect to a predetermined standard reflectance map;

(d) a stiff target adapted to be placed on the body part in a field of view including a three-dimensional feature, the stiff target having thereon a first spot of a first reflectivity and a second spot of the second reflectivity;

(e) the imaging system operating to produce a two-dimensional image of the three-dimensional feature and the stiff target;

(f) the computer being adapted to
   i. use intensity values and aspect ratio values from the first and second spots of the two-dimensional image to normalize intensity values of the two-dimensional image with respect to the predetermined standard reflectance map,
   ii. correlate the normalized intensity values of the two-dimensional image to the normalized intensity values of the normalized reference body part reflectance map to determine slant angles of the body part at pixels of the two-dimensional image,
   iii. correct a pixel dimension of each pixel in a portion of the two-dimensional image including the three-dimensional feature in accordance with the slant angle of the body part at that pixel to obtain corrected three-dimensional pixel areas, and
   iv. sum the corrected three-dimensional pixel areas to obtain the three-dimensional feature area.

15. A method of determining the area of a three-dimensional feature on a body part from a two-dimensional image thereof, comprising the steps of:

(a) providing an imaging system for producing two-dimensional image coordinate data including intensity values at each pixel, respectively, of a two-dimensional image of a body part;

(b) placing at least two stiff targets on the body part in a field of view including a three-dimensional feature, the stiff targets each having thereon a circular cutout, a first spot of a first reflectivity and a second spot of a second reflectivity;

(c) operating the imaging system to produce a two-dimensional image of the body part and the stiff targets;

(d) calculating and storing a normalized reference body part reflectance map representing a reference body part, the reference body part reflectance map including slant angles corresponding to gray scale intensity levels of images of the body part that
   (i) is obtained in conjunction with the two-dimensional image of the stiff targets each having thereon a circular cutout, a first circular spot of the first reflectivity and a second circular spot of a second reflectivity different than the first reflectivity, and
   (ii) is normalized to a standard target reflectance map using intensity values and aspect ratio values of the first and second spots of the two dimensional image;

(e) using intensity values and aspect ratio values of the first and second spots of the two dimensional image to normalize the gray level intensities of the two-dimensional image of the three-dimensional feature with respect to the predetermined standard target reflectance map;

(f) correlating the normalized intensity values of the two-dimensional image to the normalized intensity values of the normalized body part reflectance map to determine slant angles of the body part at predetermined pixels of the two-dimensional image;

(g) correcting a pixel dimension of each pixel in a portion of the two-dimensional image including the three-dimensional feature in accordance with the slant angle of the body part at that pixel to obtain corrected three-dimensional pixel areas; and (h) summing the corrected three-dimensional pixel areas to obtain the three-dimensional feature area.

16. A method of determining the area of a three-dimensional feature on a body part from a two-dimensional image thereof, comprising the steps of:

(a) providing an imaging system for producing two-dimensional image coordinate data including intensity values at each pixel, respectively, of a two-dimensional image of a body part;

(b) placing different types of stiff targets on the body part in a field of view including the feature, with at least one standard stiff target having thereon a first spot of a first reflectivity and a second spot of a second reflectivity, and at least two stiff targets each having thereon a circular cutout;

(c) operating the imaging system to produce a two-dimensional image of the body part and the stiff targets;

(d) calculating and storing a normalized reference body part reflectance map representing a reference body part, the reference body part reflectance map including slant angles corresponding to gray scale intensity levels of images of the body part that
   (i) is obtained in conjunction with the two-dimensional image of the stiff targets each having thereon a circular cutout, a first circular spot of the first reflectivity and a second circular spot of a second reflectivity different than the first reflectivity, and
   (ii) is normalized to a standard target reflectance map using intensity values and aspect ratio values of the first and second spots of the two dimensional image;

(e) using intensity values and aspect ratio values of the first and second spots of the two dimensional image to normalize the gray level intensities of the two-dimensional image of the three-dimensional feature with respect to the predetermined standard target reflectance map;

(f) correlating the normalized intensity values of the two-dimensional image to the normalized intensity values of the normalized body part reflectance map to determine slant angles of the body part at predetermined pixels of the two-dimensional image;

(g) correcting a pixel dimension of each pixel in a portion of the two-dimensional image including the feature in accordance with the slant angle of the body part at that pixel to obtain corrected three-dimensional pixel areas; and (h) summing the corrected three-dimensional pixel areas to obtain the three-dimensional feature area.

17. A method of determining the area of a three-dimensional feature on a body part from a two-dimensional image thereof, comprising the steps of:

(a) providing an imaging system for producing two-dimensional image coordinate data including intensity values at each pixel, respectively, of a two-dimensional image of a body part;

(b) placing at least 2 stiff targets on the body part in a field of view including the three-dimensional feature, the stiff targets each having thereon a circular cutout;

(c) operating the imaging system to produce a two-dimensional image of the body part and the stiff targets;

(d) calculating and storing a reference body part reflectance map unique to the two-dimensional image, the reference body part reflectance map including slant angles corresponding to gray scale intensity levels of images of the body part that are obtained in conjunction with the two-dimensional image of the stiff targets each having thereon a circular cutout;

(e) correlating the intensity values of the two-dimensional image to the intensity values of the body part reflectance map to determine slant angles of the body part at predetermined pixels of the two-dimensional image;

(f) correcting a pixel dimension of each pixel in a portion of the two-dimensional image including the three-dimensional feature in accordance with the slant angle of the body part at that pixel to obtain corrected three-dimensional pixel areas; and (g) summing the corrected three-dimensional pixel areas to obtain the three-dimensional feature area.

* * * * *